(12) United States Patent
Schembri et al.

(10) Patent No.: US 6,458,526 B1
(45) Date of Patent: Oct. 1, 2002

(54) METHOD AND APPARATUS TO INHIBIT BUBBLE FORMATION IN A FLUID

(75) Inventors: Carol T. Schembri, San Mateo, CA (US); David R. Otis, Jr., Corvallis; Philip A. Harding, Albany, both of OR (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/494,146

(22) Filed: Jan. 28, 2000

(51) Int. Cl.$^7$ .................................................. C12Q 1/00
(52) U.S. Cl. ............... 435/4; 435/287.1; 435/287.2; 435/288.4; 422/102; 436/807; 436/809; 356/246
(58) Field of Search .................. 43/4, 287.1, 287.2, 43/288.4; 422/102; 436/807, 809; 356/246

(56) References Cited

U.S. PATENT DOCUMENTS

| | | | |
|---|---|---|---|
| 5,256,535 A | 10/1993 | Ylikoski et al. | 435/6 |
| 5,622,822 A | 4/1997 | Ekeze et al. | 435/6 |
| 5,922,591 A | 7/1999 | Anderson et al. | 435/287.2 |
| 5,945,334 A | 8/1999 | Besemer et al. | 435/287.2 |
| 5,959,098 A | 9/1999 | Goldberg et al. | 536/25.3 |

Primary Examiner—David A. Redding

(57) ABSTRACT

The invention relates to an apparatus for inhibiting bubble formation during a chemical reaction. The apparatus comprises a base having a substantially planar surface with at least a portion of the surface representing a fluid contact area and a fluid comprising a liquid component in contact therewith. A cover and the base form an enclosure containing the fluid and a gas. A non-free-floating fluid-distribution member is provided that has a substantially flat surface in contact with the fluid. The member surface is disposed in an opposing and substantially parallel manner at a specified distance from fluid contact area. A gas-fluid interface having an interface radius is formed between the fluid and the gas. The apparatus also comprises means for maintaining a desired vapor pressure of the liquid component in the gas and means for immobilizing the cover with respect to the base. The interface radius is selected to result in a predetermined critical radius below which a bubble will shrink. The invention also encompasses a method for inhibiting bubble formation during a chemical reaction using the aforementioned apparatus.

50 Claims, 3 Drawing Sheets

METHOD AND APPARATUS TO INHIBIT BUBBLE FORMATION IN A FLUID

TECHNICAL FIELD

This invention relates generally to the suppression of bubble formation in a fluid having an interface with a gas. More particularly, the invention relates to a method and apparatus for containing a small quantity of fluid on a solid substrate while inhibiting bubble formation. A primary use of the invention is in solid phase chemical processes, e.g., in array hybridization.

BACKGROUND

Nucleic acid hybridization is a known method for identifying specific sequences of nucleic acids; hybridization involves base-pairing between complementary nucleic acid strands. When single-stranded nucleic acids are used as probes to identify specific target sequences of nucleic acids, probes of known sequences are exposed to and incubated in sample solutions containing sequences to be identified. If a sequence hybridizes to a probe of a known sequence, the sequence is necessarily the specific target sequence. Various aspects of this method have been studied in detail. In essence, all variations allow complementary base sequences to pair and thus form double-stranded stable molecules, and a variety of methods are known in the art to determine whether pairing has occurred, such as those described in U.S. Pat. No. 5,622,822 to Ekeze et al. and U.S. Pat. No. 5,256,535 to Ylikoski et al.

Hybridization of surface-bound probes to solution-based targets is an effective means to analyze a large number of DNA or RNA molecules in parallel. Specific probes of known sequences are attached to the surface of a solid substrate in known locations. The probes are usually immobilized on a solid support having a surface area of typically less than a few square centimeters. The solid support is typically a glass or fused silica slide which has been treated to facilitate attachment of probes. A mobile-phase sample containing labeled targets, e.g., a buffered aqueous solution containing target DNA, is contacted with and allowed to react with the surface. By detecting the labels to determine whether hybridization has occurred at specific locations, it is possible to determine the composition of the sample and the sequences of the unknown targets. Alternatively, target biomolecules may be bound to the surface while labeled probes are contained in the mobile phase. In either case, the hybridization reaction typically takes place over a time period that can be many hours, for a typical sample containing target material in the concentration range in the picomolar domain.

A number of factors contribute to the desirability of using samples that contain a small volume of fluid. First, as a general matter, the extent of the hybridization reaction is proportional to concentration. Since concentration is inversely proportional to volume, it is desirable to decrease the volume of fluid for any sample. In addition, where array technology is employed, it is now possible to attach an increasing number of distinct probes, each in a known location, on a relatively small substrate. Particularly to prevent waste of a limited supply of sample fluid, it is desirable to use only enough fluid to contact each probe feature of the array.

When an array is employed, every part of the probe-containing surface should have equivalent exposure to the target solution to ensure uniform hybridization conditions at each probe. Typically, an array is provided on a slide, and target solution is spread over the array with a cover slip. Only 10–20 $\mu$l of sample fluid is needed to cover an array in the shape of a square with sides of 20 mm in length. The fluid layer is typically 25–50 $\mu$m thick. In essence, the cover slip can be described as freely floating on the thinly spread solution and held in place only by the surface forces between the fluid and cover slip. The assembly is then placed in a humidified chamber which is in turn placed in an incubator at the desired temperature for hybridization. Hybridization is usually induced at elevated temperatures, and the humidity prevents the fluid layer from evaporating. While bubbles are generally not observed to form in the typical cover slip slide set-up, there are several problems with this assembly. The fluid layer is not always a constant thickness, resulting in more target molecules contacting some surface regions and fewer target molecules coming into contact with other surface regions. This is problematic because the extent of hybridization will vary across the surface. In addition, the assembly must be held flat and horizontal so that the cover slip does not slide off and uncover the array. Such assemblies are therefore difficult to handle and not easily adaptable to automated hybridization processes.

In the alternative, hybridizing arrays may be packaged in a sealed chamber such that sample fluid is placed in contact with the array within the chamber. Several packaging approaches have been demonstrated. U.S. patent application Ser. No. 09/299,976 describes an adjustable volume hybridization chamber. U.S. patent application Ser. No. 09/133,102 describes a centrifugal valve for containing and then controllably releasing the fluid sample. U.S. patent application Ser. No. 09/302,011 describes package solutions for annular format arrays. U.S. patent application Ser. No. 09/343,645 describes packaging solutions for multiple arrays and multiple packages. U.S. patent application Ser. No. 09/343,372 describes a reusable hybridization package. There are many advantages to packaging the arrays in sealed chambers. Since chambers containing the fluid are sealed, the risk of unacceptable fluid evaporation is eliminated or at least lowered. Packaging also allows the fluid height to be more controlled, thereby allowing for even hybridization. The ease with which packages can be handled, when compared with the floating cover slip assembly as described above, allows hybridization to be automated. In addition, packages may be designed such that the fluid is mixed within the package to ensure that no diffusion rate limited concentration gradient within the fluid develops during hybridization. The major disadvantage in using sealed packages is that bubbles tend to form in the hybridization fluids during the time it takes for hybridization to occur.

While bubbles may be employed to mix the hybridization fluid during hybridization, e.g., as described in U.S. patent application Ser. No. 09/137,963, bubbles are generally undesirable in hybridizations where a thin film of hybridization fluid is used, for a number of reasons. Bubbles are local inhomogeneities in the hybridization fluid. And if they remain substantially immobile during hybridization, the bubbles can result in uneven heat transfer and localized hot spots on the surface containing bound biomolecules. In an extreme case, bubbles may disrupt the continuity interface between the hybridization fluid and the surface containing bound probes, thereby displacing fluid away from surface-bound probes and preventing target species from contact with the probes.

There have been a number of means developed for minimizing the adverse impact of bubble formation. For example, a surfactant may be added to the hybridization solution and the solution continuously mixed to ensure that the bubbles are mobile and prevented from remaining at any particular location. In addition, U.S. Pat. No. 5,959,098 to Goldberg et al., U.S. Pat. No. 5,945,334 to Besemer et al. and U.S. Pat. No. 5,922,591 to Anderson et al. each describe other bubble management means such as employing non-parallel top and bottom surfaces in a hybridization chamber to reduce the potential of trapping the bubbles. Another such bubble management means involves moving the hybridization solution in and out of the chamber throughout the hybridization process. All these references address the problems associated with bubble formation, but do not provide a means for inhibiting bubble formation.

Thus, there is a need for a method and apparatus to inhibit bubble formation in a hybridization package adaptable for automated processing.

SUMMARY OF THE INVENTION

Accordingly, it is an object of the present invention to overcome the above-mentioned disadvantages of the prior art by providing a new and effective apparatus for inhibiting bubble formation during a chemical reaction.

It is another object of the invention to provide such an apparatus which is capable of carrying out the chemical reaction with a very small amount of fluid.

It is still another object of the invention to provide such an apparatus wherein the chemical reaction involves the hybridization of biomolecules.

It is a further object of the invention to provide a new and effective method for inhibiting bubble formation during a chemical reaction conducted on a solid surface.

Additional objects, advantages and novel features of the invention will be set forth in part in the description which follows, and in part will become apparent to those skilled in the art upon examination of the following, or may be learned by practice of the invention.

In one aspect, then, the invention relates to an apparatus for inhibiting bubble formation during a chemical reaction. The apparatus comprises a base typically having a substantially planar surface with at least a portion of the surface representing a fluid contact area and a fluid comprising a liquid component in contact therewith. A cover which sealingly contacts the base directly or indirectly about the fluid contact area forms an enclosure containing the fluid and a gas. Attached to the cover or the base is a fluid-distribution member having preferably a substantially flat surface in contact with the fluid. The member surface is disposed in an opposing manner, ideally also substantially parallel manner, at a specified distance from fluid contact area. A gas-fluid interface having an interface radius is formed between the fluid and the gas. The apparatus also comprises means for maintaining a desired vapor pressure of the liquid component in the gas and means for immobilizing the cover with respect to the base. The interface radius is selected to result in a predetermined critical radius below which a bubble will shrink. The predetermined critical radius should be equal to at least half the distance between the member surface and the base surface.

In another aspect, the invention relates to the apparatus as above wherein the fluid comprises a biomolecule. The biomolecule may be an oligonucleotide, a polynucleotide, an oligopeptide or a polypeptide. The biomolecule may be adapted to react with an array of features attached to the fluid contact area.

In another aspect, the invention relates to the apparatus as above wherein the means for maintaining the desired vapor pressure comprises a supply of the liquid component independent from the fluid in vapor communication with the interface between the fluid and gas. The supply of the liquid component may comprise the liquid component contained in a compartment located within the enclosure. In addition, the desired vapor pressure may correspond to a condition where liquid component is nearly or fully saturated in the gas. For example, the liquid component may be water and the condition may be no less than about 90% rH.

In a further aspect, the invention relates to the apparatus as above further comprising a sealable fill conduit that extends through the cover. The conduit terminates in an outlet within the enclosure. The outlet of the conduit may be substantially centrally located on the fluid-distribution member. The apparatus may further comprise a vent port located on the cover.

In still a further aspect, the invention relates to the apparatus as above wherein the fluid-distribution member comprises a plurality of openings located on the member surface to provide fluid with vapor communication with the gas to form the gas-fluid interface. The fluid-distribution member may comprise a screen. In addition, the member surface or the base surface may comprise a hydrophobic material such as a fluorinated or perfluorinated polymeric substance.

In another aspect, the invention relates to a method for inhibiting bubble formation in a chemical or a biochemical reaction. To carry out the method the following are provided: a base having a substantially planar surface representing a fluid contact area; a cover capable of sealingly contacting. the base directly or indirectly about the fluid contact area; and a fluid distribution member having a substantially flat surface. Fluid comprising a liquid component is dispensed on the fluid contact area. A cover is placed in direct or indirect sealing contact with the base to form an enclosure. A desired vapor pressure of the liquid component in the gas is effected in the enclosure. The member surface is maintained in non-free-floating contact with the fluid such that the member surface and the base surface are disposed at a specified distance of each other and in an opposing and substantially parallel manner. As a result, a gas-fluid interface is formed having a gas-fluid radius that is selected to provide a predetermined radius below which a bubble will shrink.

BRIEF DESCRIPTION OF THE DRAWINGS

The invention is described in detail below with reference to the following drawings.

DETAILED DESCRIPTION OF THE INVENTION

Overview and Definitions

Figure 1A:
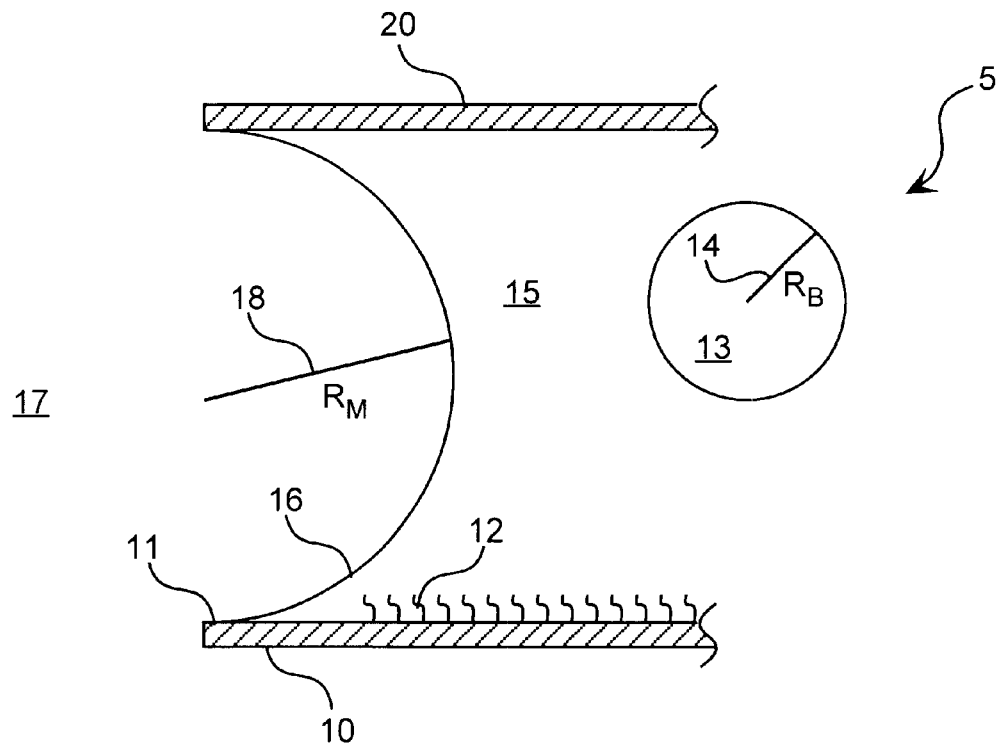
FIG. 1A schematically illustrates a cross-sectional view of a typical cover slip and slide set-up for carrying out hybridization reactions.

Before describing the present invention in detail, it is to be understood that this invention is not limited to specific compositions, reagents, process steps, or equipment, as such may vary. It is also to be understood that the terminology used herein is for the purpose of describing particular embodiments only, and is not intended to be limiting.

It must be noted that, as used in this specification and the appended claims, the singular forms "a," "an," and "the" include plural referents unless the context clearly dictates otherwise.

In describing and claiming the present invention, the following terminology will be used in accordance with the definitions set out below.

The terms "array" is used herein to refer to an ordered pattern of features, typically biomolecules, adherent to a substrate, e.g., wherein a plurality of molecular probes is bound to a substrate surface and arranged in a spatially defined and physically addressable manner. Such probes may be comprised of oligonucleotides, peptides, polypeptides, proteins, antibodies, or other molecules used to detect sample molecules in a sample fluid.

The term "biomolecule" as used herein refers an organic molecule that may be found in a living organism or synthetically produced. Typically, biomolecules are large and may have a complementary counterpart. Examples of biomolecules include but are not limited to nucleotidic molecules such as oligonucleotides and polynucleotides and peptidic molecules such as oligopeptides and polypeptides.

The term "bubble" as used herein refers to a volume of gas generally in the shape of a sphere within a fluid wherein the gas comprises vapors of the liquid component of the fluid, dissolved gas in the fluid or a combination thereof.

The term "critical radius" as used herein refers to the distance between the center and surface of a dimensionally stable bubble. A bubble having a radius greater than the critical radius in a fluid will tend to expand. A bubble having a radius lower than the critical radius will tend to shrink.

The term "chemical reaction" as used herein refers to a reaction involving the formation or breaking of ionic, covalent, polar, hydrogen or other type of bond of a chemical of biochemical species. Unless otherwise stated, the chemical reaction occurs at or near a surface.

The term "contact angle" as used herein relates to a measure of wetting of a solid surface by a liquid. The contact angle refers to the angle between a flat solid surface and the tangent to the liquid surface at the contact point. Contact angles may vary from 0° to 180°, inclusive. Lower contact angles indicate a high degree of wetting of the solid surface by the liquid. Non-wetting surfaces exhibit a high contact angle with respect to the liquid. A contact angle of 90° is defined as the boundary between non-wetting and wetting. A "hydrophobic" surface is one which exhibits a contact angle greater than 90° with respect to water. A surface is said to be "lyophobic" with respect to a liquid when the surface exhibits a contact angle greater than 90° with respect to the liquid. A high "lyophobicity" results in a large contact angleln increasing contact angle.

The term "fluid" as used herein refers to a material that is not purely gaseous which tends to flow to conform to the outline of its container. Unless otherwise stated, the fluids described herein comprise a liquid and may contain solvated gas or fully solvated, partially solvated or suspended solids.

The term "immobilizing means" as used herein means any object or method effective to render two objects substantially immovable with respect to each other.

Immobilizing means include, but are not limited to, clamps, clips, springs, brackets, housings with screws, hinged devices with tightening means, and the like.

The term "hybridization" is used in its conventional sense to refer to binding between complementary or partially complementary molecules, as between the sense and antisense strands of double-stranded DNA. Such binding is commonly non-covalent binding, and is specific enough that such binding may be used to differentiate between highly complementary molecules and others less complementary. Examples of highly complementary molecules include complementary oligonucleotides, DNA, RNA, and the like, which comprise a region of nucleotides arranged in the nucleotide sequence that is exactly complementary to a probe; examples of less complementary oligonucleotides include ones with nucleotide sequences comprising one or more nucleotides not in the sequence exactly complementary to a probe oligonucleotide.

The term "monomer" as used herein refers to a chemical entity that can be covalently linked to one or more other such entities to form an oligomer. Examples of "monomers" include nucleotides, amino acids, saccharides, peptides, and the like. In general, the monomers used in conjunction with the present invention have first and second sites (e.g., C-termini and N-termini, or 5' and 3' sites) suitable for binding to other like monomers by means of standard chemical reactions (e.g., condensation, nucleophilic displacement of a leaving group, or the like), and a diverse element which distinguishes a particular monomer from a different monomer of the same type (e.g., an amino acid side chain, a nucleotide base, etc.). The initial substrate-bound monomer is generally used as a building-block in a multi-step synthesis procedure to form a complete ligand, such as in the synthesis of oligonucleotides, oligopeptides, and the like.

The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. Moreover, the terms "nucleoside" and "nucleotide" include functional analogs (whether synthetic or naturally occurring) of such sub units which in the polymer form (as a polynucleotide) can hybridize with naturally occurring polynucleotides in a sequence specific manner analogous to that of tow naturally occurring polynucleotides. For example, these include the sub-units of PNA and other polynucleotides as described in U.S. Pat. No. 5,948,902 and references cited therein (all of which are incorporated herein by reference), regardless of the source.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides, polyribonucleotides, other polynucleotides which are or C-glycosides of a purine or pyrimidine base, polypeptides, polysaccharides, and other chemical entities that contain repeating units of like chemical structure. In the practice of the instant invention, oligomers will generally comprise about 10 or more monomeric units.

The term "probe" as used herein means a biomolecule of known identity that is typically but not necessarily adherent to a substrate or a base member of a hybridization package.

The term "sample" as used herein relates to a material or mixture of materials, at least partially in fluid form, containing one or more components of interest.

The term "surface tension" as used herein means the reversible work required to increase the surface of a liquid by a unit area.

The term "surfactant" is used herein in its conventional sense to refer to a compound that effects reduction in the surface tension in a fluid and promotes the wetting of surfaces by the fluid. Examples of surfactants include anionic, cationic, amphoteric and nonionic surfactants.

The term "target" refers to a known or unknown molecule in a sample, which will hybridize to a probe if the target molecule and the molecular probe contain complementary regions. In general, the target molecule is a "biopolymer," i.e., an oligomer or polymer such as an oligonucleotide, a peptide, a polypeptide, a protein, an antibody, or the like.

The present invention is directed to an apparatus for inhibiting bubble formation in a fluid within a sealed package adaptable for automated processing. Unlike ordinary devices in which deleterious effects of bubbles are reduced through management of the bubbles after their formation, the invention inhibits bubble formation through the control of the critical radius of the bubble. The critical radius is controlled by maintaining a desired vapor pressure of a liquid component of fluid in a gas and by controlling the radius of the interface between the fluid and the gas. The sealed package provides greater ease in handling than an ordinary hybridization set-up which provides a free-floating cover slip on a slide. In addition, the invention is also directed to a method for inhibiting bubble formation.

The critical radius is central to understanding bubble formation and is described herein with reference with to the figures. It is to be noted that the figures are not to scale, and, in particular, certain of the dimensions may be exaggerated to clarity of presentation. FIG. 1 schematically illustrates a cross-sectional view of a conventional slide and cover slip set-up 5 for carrying out hybridization reactions. This set-up 5 is usually assembled in air 17. A slide 10 having an upper surface 11 is provided. Attached to the upper surface is a plurality of probes 12 in contact with a sample fluid 15 containing a liquid component, typically water. Typically, solutions are not degassed and are assumed to have a uniform density. A representative bubble 13 having a bubble radius 14, $R_B$, is located within the fluid 15. It is assumed that bubbles already exist in the fluid without having to be nucleated. It is also assumed that these bubbles may grow or shrink by diffusion of air though the fluid. It is further assumed that air can be treated as a single gas, with properties of nitrogen gas such as diffusivity, solubility, molecular weight, etc. Once a cover slip 20 is placed on the fluid in a free floating manner to reduce the amount of fluid needed to contact all probes on the upper surface of the slide, a fluid-air interface 16 is formed between the cover slip 20 and the slide 10. As shown, the fluid-air interface 16 is in the form of a meniscus having a meniscus radius 18, $R_M$.

Because the above set-up is subject to gas diffusion between the air and the gas within a bubble, a mathematical model that approximates the above set-up can be derived in part from Fick's Law. Fick's Law generally provides that diffusion of a gas in the fluid should be proportional to the concentration gradient of the gas in the fluid. In addition, Henry's Law states that the amount of gas that dissolves into a liquid is proportional to the partial pressure of the gas at the surface of the liquid. For the above set-up, it is assumed that convective mass transfer does not occur in the set-up and that air can be treated as a single gas. Thus, diffusion can be expressed as a function of the gaseous partial pressures as follows:

$$J = 31\ DS(P_{N1} - P_{N2})$$

where J is the flux of air, D is a diffusion constant, S is a shape factor specific to the geometry of the set-up, and $P_{N1}$ and $P_{N2}$ are the partial pressures of the air or the vapor component of the humidified air (assuming that the liquid is water) at the surface of the liquid and within the bubble, respectively. If $P_{N1}$ is equal to $P_{N2}$, net flux is zero, and a bubble will neither expand nor shrink. Similarly, if $P_{N1}$ is smaller than $P_{N2}$, the bubble will shrink.

Where the liquid component is water, overall air pressure $P_1$ is the sum of partial pressure of non-water components, $P_{N1}$ and the partial vapor pressure of water $P_{H2O}$. That is:

$$P_1 = P_{N1} + P_{H2O}.$$

$P_{H2O}$ can be expressed as the product of the relative humidity, rH, and the maximum pressure of water at a specific temperature of interest, $P_{VAP}$. Thus, $$P_1 = P_{N1} + rHP_{VAP}.$$

Since the fluid is not degassed, air pressure within the bubble, $P_2$, is the sum at partial vapor pressure of non-water components, $P_{N2}$, and the partial vapor pressure of the water. It is assumed that the air within the bubble quickly becomes saturated with the vapors of the liquid component of the fluid and thus:

$$P_2 = P_{N2} + P_{VAP}.$$

In the alternative, the pressure in the bubble can be expressed as a function of surface tension of the fluid, σ, the radius of the bubble, $R_B$, and an absolute back pressure, $P_{absback}$, imposed on the fluid as follows:

$$P_2 = 2\sigma/R_B + P_{absback}.$$

The absolute back pressure is a function of the overall air pressure, the surface tension, contact angle as defined above and the radius of the meniscus formed by the air-fluid interface and can be expressed as:

$$P_{absback} = P_1 - \sigma \cos \theta / R_M$$

where θ is the contact angle and $R_M$ is the radius of the air-fluid interface. Thus, $$P_2 2\sigma/R_B + P_1 - \sigma \cos \theta / R_M$$

When $P_{N1}$ is equal to $P_{N2}$, $R_B$ becomes the critical bubble radius, $R_C$. Bubbles having a larger radius will grow; bubbles having a smaller radius will shrink and eventually collapse. The critical bubble radius can be expressed as follows:

$$R_C = \frac{2\sigma}{(\sigma \cos\theta / R_M) + (1 - rH)P_{VAP} + K} \quad (I)$$

where K is a correction factor that accounts for pressure effects from surface curvature as θ approaches 90° and rH approaches 100%. Ordinarily, K is negligible and can be approximated as zero.

When a slide and cover slip set-up are employed wherein θ is zero, i.e., the fluid completely wets the surfaces of the slide and cover slip, and the set-up is placed in a chamber with 100% rH, it is apparent that the critical bubble diameter for a bubble in a cover slip and slide hybridization set-up is twice the distance between the cover slip and the array surface. Since practically no bubble can be formed within the gap that has a diameter that is twice the distance of the gap, any tiny bubble that happens to be in the solution in such a set-up will shrink and disappear.

Figure 1B:
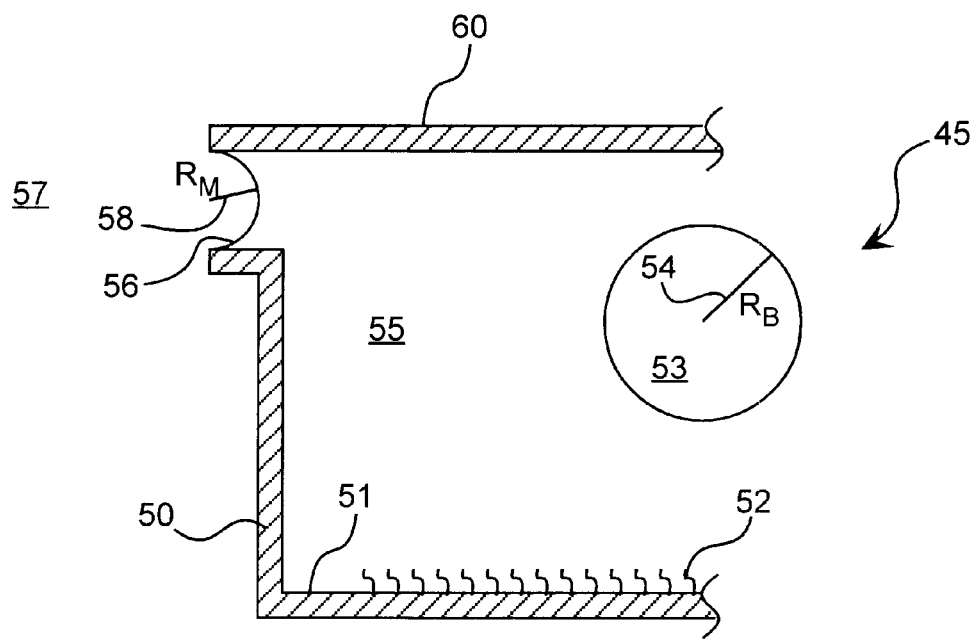
FIG. 1B schematically illustrates a cross-sectional view of an imperfectly sealed chamber of a typical hybridization package.

In contrast, FIG. 1B schematically illustrates a cross-sectional view of a conventional nominally sealed chamber of a hybridization package 45. Analogous to the slide 10 in FIG. 1A, a base 50 having an upper surface 51 is surface is provided.

Attached to the upper surface is a plurality of probes 52 in contact with a sample fluid 55 containing a liquid component, typically water. Again, solutions are typically not degassed. A representative bubble 53 having a bubble radius 54, $R_B$, is located within the fluid 55. When properly designed and assembled, a cover member 60 is placed on the fluid and a seal is created between the base and the cover. However, if the seal is imperfect, a fluid-air interface 56 is formed between the cover member 60 and the base 50. As shown, the fluid-air interface 56 is in the form of a meniscus having a meniscus radius 57, $R_M$. Because this meniscus has a very small radius of curvature, the critical radius is small since a large pressure drop is created on the fluid near it. This pressure drop allows tiny bubbles to be stable and grow. In addition, since the packages are not designed to leak, the environment around the package is typically not humidified, while the air inside any bubble is fully saturated. If the total pressure inside the bubble and outside the package is the same, the difference in vapor pressure in the two locations must lead to a difference in air pressures. Therefore, the air partial pressure outside the system will be higher than the air partial pressure diinside the bubble. This gradient will allow bubbles to grow.

In sum, Equation (I) describes the critical radius as a function of various factors. These factors include but are not limited to: the contact angle between the fluid and the solid surfaces, the radius of the air-fluid interface, and the content of the liquid component in the vapor form in the air. It is evident, then, that for a fluid having a specific composition and therefore a specific surface tension and vapor pressure at a set temperature, the critical bubble radius can be controlled. It is also notable that larger critical bubble radii are preferred over smaller ones. Thus, each factor can be independently manipulated to increase the critical bubble radius even if absolute control overall all factors is not achievable for any reason. Thus, for example, from Equation (I), it is apparent that the critical bubble radius can be increased by increasing the contact angle, by increasing the radius of the air-fluid interface, or by increasing the relative humidity in the air. It is important to keep in mind, though, that the equation is only an approximation of a generalized chemical reaction set-up. However, one of ordinary skill in the art can determine or control the critical radius for any particular system by routine experimentation given the guidance provided by the equation and other disclosure provided herein. For example, surface tension of the fluid can be adjusted by adding a small amount of surfactant that is compatible with the desired chemical reaction.

Figure 2:
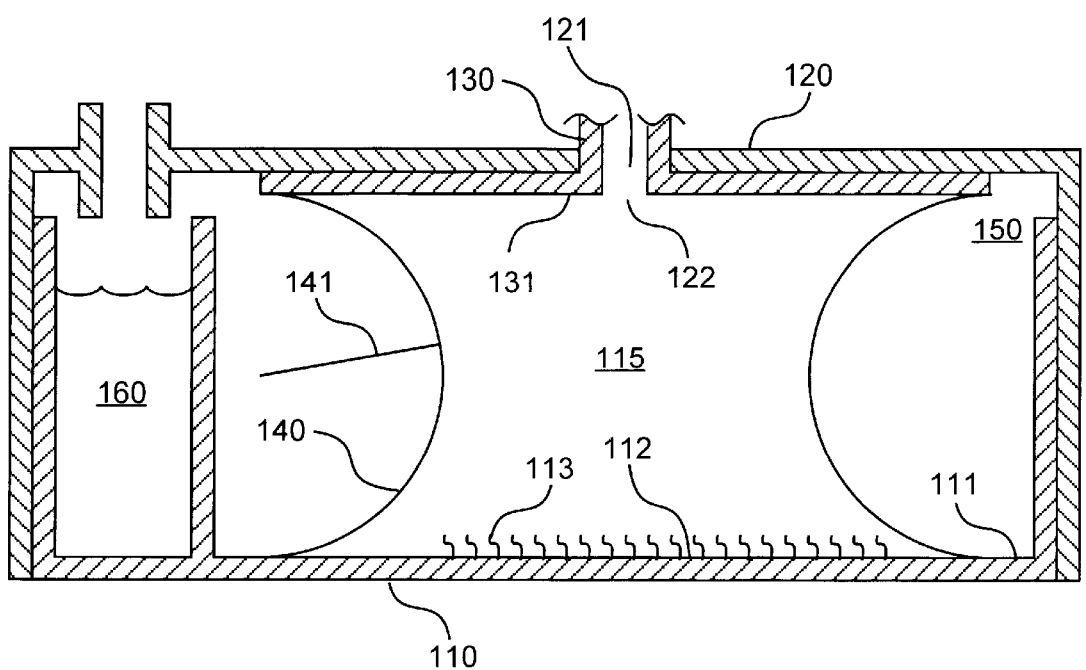
FIG. 2 schematically illustrates a cross-sectional view of a version of the apparatus of the present invention wherein the gas-fluid interface is located between the fluid-distribution member and the base.

An embodiment of the invention is now described in detail herein with reference to FIG. 2. From this description of the embodiment and the above teaching regarding the critical bubble formation radius, it is apparent to one of ordinary skill that a method for inhibiting bubble formation in a chemical reaction is also described. FIG. 2 schematically illustrates a cross-sectional view of an apparatus 100 of the present invention. The apparatus comprises a base 110 having a substantially planar surface 111 with at least a portion of the surface representing a fluid contact area 112.

Typically, for hybridization, a plurality of probe biomolecules 113 in an array is covalently or otherwise attached to the base surface within the fluid contact area 112. A sample fluid 115 comprising target biomolecules and a liquid component, typically water, is placed in contact with the fluid contact area 112 of the base surface 111. The volume of fluid is typically small, usually containing up to only about 200 µl of the liquid component. In addition, the ratio of volume of the fluid to the fluid contact area is typically small. For a contact area of about 400 square millimeters, usually only 10–20 µl of fluid is used. A cover 120 is provided which contacts the base 110 about the fluid contact area. As shown, the cover directly contacts the base such that a seal is formed. However, the cover may indirectly contact the base, i.e., contact another solid member which in turn contacts the base. In either case, a substantially gas-tight enclosure containing the fluid and a gas is formed. "Substantially gas-tight" means that the vapor pressure of the liquid component within the enclosure can be maintained as described below. As shown, the enclosure 150 is formed by the base and the cover 120 which sealingly contacts with base about the fluid. Since one aim of the invention is to provide in ease in handling, the invention also provides immobilizing means for immobilizing the cover with respect to the base (not shown).

Also provided is a fluid distribution member 130 having a substantially flat surface 131. The purpose of the fluid distribution member is similar to that of the cover slip for the typical cover slip and slide set-up—to ensure that a small amount of the sample fluid is spread in a manner such that all probe biomolecules within the fluid contact area are, as a general matter, equivalently exposed to the sample fluid. The flat surface of the fluid distribution member is contacted with fluid and secured or mounted in an opposing and substantially parallel manner at a specified distance from fluid contact area 112. As shown, the member is disposed in a non-free-floating manner on the fluid. The member 130 is secured to a conduit 121 that is rotatably extends through the cover 120. The interface between the conduit and the cover provides a substantially gas-tight seal. A terminus of the conduit forms an outlet 122 that is substantially centrally located on the fluid-distribution member 130 and within the enclosure. Through this conduit, the sample fluid may be dispensed onto the fluid contact area of the base. The conduit is sealable such that the enclosure can be maintained substantially gas-tight. By rotating the conduit, the member is also rotated to induce convective mixing in the fluid. Optionally, a vent port may be disposed on the cover to reduce unwanted gas pressure buildup from introduction of the fluid into the sealed enclosure. Alternatively, the member may be attached to the base or some other solid surface within the enclosure such that the member is rigidly and substantially mounted over the array at a specified distance, e.g., 10–100 microns or more preferably 25–50 microns. In either case, the apparatus 100 is typically assembled under ordinary atmospheric conditions. However, any atmosphere that will not interfere with the desired reactions within the fluid are suitable. Such an atmosphere may contain inert gases such as nitrogen, argon, helium and the like.

Once the member surface is disposed with respect to the array and the fluid in the manner as described above, a gas-fluid interface 140 is formed. As shown in FIG. 2, the gas-fluid interface 140 is disposed between the base surface 111 and the fluid-distribution member surface 131. In this case, both the member surface and the base surface are hydrophillic, and a meniscus is formed at the edge. The radius of the meniscus formed by the gas-fluid interface is designated as an interface radius 141.

As discussed above, the critical radius is a function of the contact angle between the fluid and the solid surfaces. It is evident from the above equation that the critical radius is generally proportional to the contact angle between the fluid and the surface of the base and the fluid distribution member. To increase the critical radius, then, the contact angle may be increased by ensuring that the fluid distribution and the base surfaces that contact the fluid repel the fluid, i.e., that the surfaces are lyophobic with respect to the fluid. For example, if a liquid component of the fluid is water, then the fluid distribution and base surfaces should comprise a hydrophobic material at least in the vicinity of the fluid-gas interface. In addition, a high degree of lyophobicity is preferred. For example, it is preferred that the fluid and the surface form a contact angle of 90 to about 180°. It is more preferred that the contact angle is from about 120° to about 180°. Still more preferred is a contact angle of about 150° to 180°. This hydrophobic material is particularly useful when control over the relative humidity in the gas is not absolute and can counteract the effects of a decreasing relative humidity in the gas if the apparatus is not completely sealed. The fluid distribution member may be made from a hydrophobic material or have a coating of hydrophobic material that serves as the surface. Suitable hydrophobic materials include, but are not limited to, polymers such as silicones, polyalkenes, fluorinated polymers and perfluorinated polymers. Fluorinated polymers such as polyvinyl fluoride and polyvinylidene fluoride and perfluorinated polymers such as polytetrafluoroethylene exhibit a high degree of hydrophobicity and are thus preferred polymers. It is important to keep in mind that the hydrophobic material as well as other components of the apparatus of the invention must be able to withstand the conditions under which the desired chemical or biochemical reaction is carried out.

Also provided is a vapor maintenance means for maintaining a desired vapor pressure of the liquid component in the gas. As illustrated in FIG. 2, such means may comprise a supply of the liquid component independent from the fluid in vapor communication with the interface between the fluid and gas. The supply of the liquid component is contained in a compartment 160 located within the enclosure 150. It is desirable for the supply to contain a higher concentration of the liquid than the hybridization fluid. Such a supply has a higher vapor pressure than the hybridization fluid and will preferentially evaporate. In this case, an environment is created around the hybridization region in the enclosure such that the gas is nearly or fully saturated with the vapors of the liquid component of the sample fluid. To maintain this environment, the enclosure is substantially sealed.

While vapor maintenance means for maintaining a desired vapor pressure of the liquid component in the gas can be located within the enclosure, it is also possible that at least a portion of such means is located outside the enclosure. For example, a supply of the liquid component can be provided from a source that is in vapor communication with respect to the enclosure. The supply of liquid can be subjected to heating, atomization, or other conditions such that the liquid is vaporized and transported into the enclosure. Such heating, atomization or other conditions can be imposed through a computerized or other control mechanism known to one of ordinary skill in the art. It is also possible that the vapor maintenance means may be the sample fluid itself provided that the enclosure is sufficiently small and adequately sealed to ensure that the concentration of the solid content in the fluid is not adversely affected by the evaporation of the liquid component to form the desired vapor pressure in the enclosure. In any case, with or without a vapor maintenance means, it is desired that the partial vapor pressure of the liquid component in the gas of the fluid is not substantially decreased, i.e., the partial vapor pressure of the liquid component is steady state or increasing. Decreasing partial pressure tends to hasten the evaporation of the fluid. It is preferred that the desired vapor pressure corresponds to a condition where the gas is nearly or fully saturated with the liquid component of the fluid. Where the liquid component is water, it is desirable that the condition is no less than about 90% rH.

Figure 3:
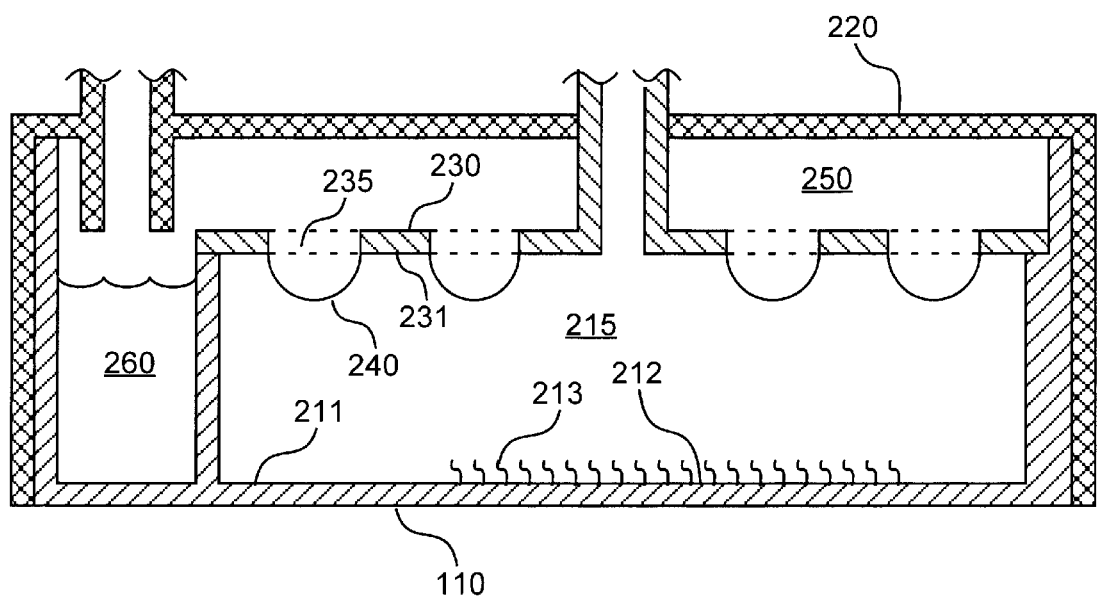
FIG. 3 schematically illustrates a cross-sectional view of a version of the apparatus of the present invention wherein the fluid-air interface is located in the openings within the member.

The components of the device are assembled such that the interface radius results in a critical radius below which a bubble in the fluid will shrink. While FIG. 2 illustrates a version of the inventive apparatus wherein the gas-fluid interface is located between the fluid distribution member and the base, the interface may be located elsewhere, as illustrated in FIG. 3. In the embodiment illustrated in FIG. 3, the apparatus comprises a base 210 having a substantially planar surface 211 with at least a portion of the surface representing a fluid contact area 212. A sample fluid 215 comprising target biomolecules and a liquid component, typically water, is placed in contact with the fluid contact area 212 of the base surface 211. Covalently or otherwise attached to the contact area is an array of probe biomolecules 213. A cover 220 is provided which contacts the base 210 about the fluid contact area. As shown, the cover directly contacts the base such that a substantially gas-tight enclosure containing the fluid and a gas is formed. A supply of the liquid component is contained in a compartment 260 located within the enclosure 250.

Also provided is a fluid distribution member 230 having a substantially flat surface 231. As shown, the fluid distribution member 230 is in the form of a screen comprising a plurality of through openings 235 to provide fluid with vapor communication with the gas and thus form the gas-fluid interface 240. The size of the openings in the screen is roughly the same size as the distance between the screen and the array. When a fluid is dispensed on the screen, the screen can draw the fluid toward the array by capillary action and then keep the fluid in place. It is evident that the gas-fluid interfaces are formed within the openings in the screen. Because the openings are relatively large, the critical bubble size is also large. In addition, since the screen is mounted, it cannot slip as the array is moved around during automatic handling processes.

It is to be understood that while the invention has been described in conjunction with preferred specific embodiments thereof, the foregoing description is intended to illustrate and not limit the scope of the invention. For example, while the inventive apparatus may be used to inhibit bubble formation in hybridization reactions, the apparatus may be also used for other reactions that employ a small amount of fluid. Other aspects, advantages and modifications within the scope of the invention will be apparent to those skilled in the art to which the invention pertains.

All patents, patent applications, and publications mentioned herein are hereby incorporated by reference in their entireties.

What is claimed is:

1. An apparatus for inhibiting bubble formation during a chemical reaction, comprising:
    a base having a surface with at least a portion of the surface representing a fluid contact area;
    a fluid comprising a liquid component in contact with the fluid contact area;
    a cover which forms an enclosure with the base, which contains the fluid and a gas wherein the fluid and the gas form a gas-fluid interface having an interface radius;
    a fluid distribution member which may or may not be part of the cover having a surface in contact with the fluid, wherein the member surface is disposed in an opposing and non-free-floating manner with respect to the base surface at a predetermined distance from the fluid contact area; and
    vapor maintenance means for maintaining a desired vapor pressure of the liquid component in the gas,
    wherein the interface radius formed at the desired vapor pressure results in a predetermined critical radius below which a bubble in the fluid will shrink.

2. The apparatus of claim 1, wherein the predetermined critical radius is at least half the specified distance between the member and base surfaces.

3. The apparatus of claim 1, wherein the fluid contains a biomolecule.

4. The apparatus of claim 3 wherein the biomolecule is an oligonucleotide, a polynucleotide, an oligopeptide or a polypeptide.

5. The apparatus of claim 4 wherein the biomolecule is synthetic.

6. The apparatus of claim 1, wherein an array of features is attached to the base surface within the fluid contact area.

7. The apparatus of claim 6, wherein the array is covalently attached to the base surface.

8. The apparatus of claim 1, wherein the means for maintaining the desired vapor pressure comprises a supply of the liquid component independent from the fluid in vapor communication with the interface between the fluid and gas.

9. The apparatus of claim 8, wherein the supply of the liquid component is contained in a compartment located within the enclosure.

10. The apparatus of claim 1, wherein the desired vapor pressure corresponds to a condition where the liquid component is nearly or fully saturated in the gas.

11. The apparatus of claim 10, wherein the liquid component is water.

12. The apparatus of claim 11, wherein the condition is no less than about 90% rH.

13. The apparatus of claim 1, further comprising a sealable fill conduit extending through the cover and having an outlet within the enclosure.

14. The apparatus of claim 13, wherein the outlet of the conduit is substantially centrally located on the fluid distribution member.

15. The apparatus of claim 13, further comprising a vent port located on the cover.

16. The apparatus of claim 1, wherein the fluid distribution member comprises a plurality of openings located on the member surface to providing the fluid vapor communication with the gas to form the gas-fluid interface.

17. The apparatus of claim 16, wherein the fluid distribution member comprises a screen.

18. The apparatus of claim 1, wherein the member surface, the base surface or both comprise a hydrophobic material.

19. The apparatus of claim 18, wherein the hydrophobic material is a fluorinated polymeric substance.

20. The apparatus of claim 19, wherein the polymeric substance is perfluorinated.

21. The apparatus of claim 1, wherein the gas comprises nitrogen.

22. The apparatus of claim 1, wherein the fluid contains up to about 200 $\mu$l of liquid.

23. The apparatus of claim 1 further comprising immobilizing means for immobilizing the cover with respect to the base.

24. A method for inhibiting bubble formation during a chemical reaction, comprising the steps of:
    (a) providing:
        (i) a base having a base surface representing a fluid contact area;
        (ii) a cover capable of forming an enclosure with the base; and
        (iii) a fluid distribution member having a member surface;
    (b) dispensing a fluid comprising a liquid component on the fluid contact area;
    (c) forming an enclosure with the base and cover that contains a gas and the fluid;
    (d) effecting a desired vapor pressure of the liquid component in the gas in the enclosure;
    (e) maintaining the member surface in non-free-floating contact with the fluid such that the member surface and the base surface are disposed at a predetermined distance of each other and in an opposing manner; and
    (f) forming a gas-fluid interface having an interface radius that is selected to provide a predetermined critical radius below which a bubble will shrink.

25. The method of claim 24, wherein the predetermined critical radius is at least half the distance between the member surface and the base surface.

26. The method of claim 24, wherein the fluid comprises a biomolecule.

27. The method of claim 26 wherein the biomolecule is an oligonucleotide, a polynucleotide, an oligopeptide or a polypeptide.

28. The method of claim 24 wherein the biomolecule is synthetic.

29. The method of claim 24, wherein an array of features is attached to the base surface within the fluid contact area.

30. The method of claim 29, wherein the array is covalently attached to the base surface.

31. The method of claim 24, wherein step (d) comprises providing means for maintaining the desired vapor pressure comprises a supply of the liquid component independent from the fluid in vapor communication with the interface between the fluid and gas.

32. The method of claim 31, wherein the supply of the liquid component is contained in a compartment located within the enclosure.

33. The method of claim 24, wherein the desired vapor pressure corresponds to a condition where the liquid component is nearly or fully saturated in the gas.

34. The method of claim 33, wherein the liquid component is water.

35. The method of claim 34, wherein the condition is no less than about 90% rH.

36. The method of claim 24, wherein step (a) further comprises providing a sealable fill conduit extending through the cover and having an outlet within the enclosure.

37. The method of claim 36, wherein the outlet of the conduit is substantially centrally located on the fluid distribution member.

38. The method of claim 36, wherein step (a) further comprises providing a vent port located on the cover.

39. The method of claim 24, wherein the fluid distribution member comprises a plurality of openings located on the member surface to providing the fluid vapor communication with the gas to form the gas-fluid interface.

40. The method of claim 39, wherein the fluid distribution member comprises a screen.

41. The method of claim 24, wherein the member surface, the base surface, or both comprises a hydrophobic material.

42. The method of claim 41, wherein the hydrophobic material is a fluorinated polymeric substance.

43. The method of claim 42, wherein the polymeric substance is perfluorinated.

44. The method of claim 24, wherein the gas comprises nitrogen.

45. The method of claim 24, wherein the fluid contains up to about 200 $\mu$l of liquid.

46. A method for carrying out a chemical reaction, comprising:
 (a) providing:
  (i) a base having a base surface representing a fluid contact area;
  (ii) a cover capable of forming an enclosure with the base; and
  (iii) a fluid distribution member having a member surface;
 (b) dispensing a fluid comprising a liquid component on the fluid contact area;
 (c) forming an enclosure with the cover and the base that contains the fluid and a gas;
 (d) effecting a desired vapor pressure of the liquid component in the gas in the enclosure;
 (e) maintaining the member surface in non-free-floating contact with the fluid such that the member surface and the base surface are disposed at a specified distance of each other and in an opposing and substantially parallel manner; and
 (f) forming a gas-fluid interface having a gas-fluid radius that is selected to provide a predetermined critical radius below which a bubble will shrink;
 (g) applying heat to maintain the fluid at a substantially constant elevated temperature for a specified amount of time.

47. An apparatus for inhibiting bubble formation during a chemical reaction, comprising:
 a base having a surface with at least a portion of the surface representing a fluid contact area;
 a fluid comprising a liquid component in contact with the fluid contact area;
 a cover which forms an enclosure with the base, which contains the fluid wherein the fluid and a gas form a gas-fluid interface having an interface radius; and
 a fluid distribution member which may or may not be part of the cover having a surface in contact with the fluid, wherein the member surface is disposed in an opposing and non-free-floating manner with respect to the base surface at a predetermined distance from the fluid contact area, and further wherein the member surface, the base surface or both are lyophobic with respect to the fluid and the gas-fluid interface having an interface radius formed from contact with any lyophobic surface and which results in a predetermined critical radius below which a bubble in the fluid will shrink.

48. An apparatus for inhibiting bubble formation during a chemical reaction, comprising:
 a base having a surface with at least a portion of the surface representing a fluid contact area;
 a fluid comprising a liquid component in contact with the fluid contact area;
 a cover which forms an enclosure with the base, which contains the fluid; and
 a fluid distribution member which may or may not be part of the cover having:
  a surface that is disposed in an opposing and non-free-floating manner with respect to the base surface at a predetermined distance from the fluid contact area and that is in contact with the fluid; and
  a plurality of openings located on the surface to provide communication between a gas and the liquid to form a gas-fluid interface having an interface radius that results in a predetermined critical radius below which a bubble in the fluid will shrink.

49. The apparatus of claim 48, wherein the fluid distribution member comprises a screen.

50. An apparatus for inhibiting bubble formation during a chemical reaction, comprising:
 a base having a surface with at least a portion of the surface representing a fluid contact area;
 a fluid comprising a liquid component in contact with the fluid contact area;
 a cover which forms an enclosure with the base, the enclosure containing the fluid wherein a gas containing the liquid component as a vapor at a substantially non-decreasing partial pressure and the fluid form a gas-fluid interface having an interface radius; and
 a fluid distribution member which may or may not be part of the cover having a surface in contact with the fluid, wherein the member surface is disposed in an opposing and non-free-floating manner with respect to the base surface at a predetermined distance from the fluid contact area and further wherein the interface radius formed results in a predetermined critical radius below which a bubble in the fluid will shrink.

* * * * *